United States Patent [19]

Johansson et al.

[11] Patent Number: 5,036,071
[45] Date of Patent: Jul. 30, 1991

[54] DERIVATIVES OF PURINE

[75] Inventors: Karl N. G. Johansson, Enhörna; Zsuzsanna M. I. Kovacs, Södertälje; Björn G. Lindborg, Älvsjö; Göran B. Stening, Södertälje, all of Sweden

[73] Assignee: Medivir AB, Huddinge, Sweden

[21] Appl. No.: 147,051

[22] Filed: Jan. 22, 1988

Related U.S. Application Data

[63] Continuation-in-part of Ser. No. 22,569, Mar. 9, 1987, abandoned, which is a continuation of Ser. No. 807,853, Dec. 11, 1985, abandoned.

[30] Foreign Application Priority Data

Dec. 21, 1984 [SE] Sweden .................. 8406538

[51] Int. Cl.$^5$ .............. C07D 473/18; A61K 31/52
[52] U.S. Cl. .................. 514/261; 544/276; 544/277
[58] Field of Search .......... 544/277, 276; 514/261

[56] References Cited

U.S. PATENT DOCUMENTS 4,609,662 9/1986 Krenitsky ............. 514/262
4,798,833 1/1989 Johansson et al. .

FOREIGN PATENT DOCUMENTS 0182024 9/1985 European Pat. Off. .
0158847 10/1985 European Pat. Off. .
2130204A 10/1982 United Kingdom .
21302044 5/1984 United Kingdom .

Primary Examiner—Nicholas S. Rizzo
Attorney, Agent, or Firm—Birch, Stewart, Kolasch & Birch

[57] ABSTRACT

Antivirally active compounds of the formula

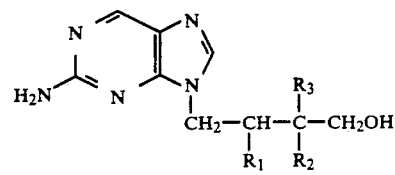

wherein
$R_1$ is hydrogen or hydroxymethyl;
$R_2$ is hydrogen, hydroxy or hydroxymethyl;
$R_3$ is hydrogen; or $R_1$ and $R_3$ together constitute an additional carbon-carbon bond;

with the proviso that when $R_1$ is hydrogen then $R_2$ is hydroxy or hydroxymethyl, that when $R_1$ is hydroxymethyl then $R_2$ is hydrogen and that when $R_2$ is hydroxy then $R_1$ is hydrogen; and physiologically acceptable salts; geometric or optical isomers thereof; processes for preparation of said compounds, pharmaceutical preparations containing the compounds, methods for treatment of virus infections and medical use of the compounds.

23 Claims, 1 Drawing Sheet

FIG. 1

DERIVATIVES OF PURINE

This application is a continuation-in-part of application Ser. No. 22,569, filed on Mar. 9, 1987 now abandoned, which in turn is a continuation of application Ser. No. 807,853 filed Dec. 11, 1985 now abandoned.

DESCRIPTION

1. Field of the Invention

The present invention relates to novel derivatives of purine, methods for their preparation, novel pharmaceutical compositions and to a method for selectivity combating viruses, such as herpes viruses, etc., which can cause various diseases in animals including man. Such diseases include both common infections and neoplastic diseases, i.e. cancer.

2. Background of the Invention

The effects of viruses on bodily functions is the end result of changes occurring at the cellular and subcellular levels. The pathogenic changes at the cellular level are different for different combination of viruses and host cells. While some viruses cause a general destruction (killing) of certain cells, other may transform cells to a neoplastic state.

Important common viral infections are herpes dermatitis (including herpes labialis), herpes keratitis, herpes genitalis, herpes zoster, herpes encephalitis, infectious mononucleosis and cytomegalovirus infections all of which are caused by viruses belonging to the herpes virus group. Other important viral diseases are influenza A and B which are caused by influenza A and B virus respectively. Another important common viral disease is viral hepatitis and especially hepatitis B virus infections are widely spread. Effective and selective antiviral agents are needed for the treatment of these diseases as well as for other diseases caused by viruses.

Several different viruses of both DNA and RNA type have been shown to cause tumors in animals. The effect of cancerogenic chemicals can on animals result in activation of latent tumor viruses. It is possible that tumor viruses are involved in human tumors. The most likely human cases known today are leukemias, sarcomas, breast carcinomas, Burkitt lymphomas, nasopharyngeal carcinomas and cervical cancers where RNA tumor viruses and herpes viruses are indicated. This makes the search for selective inhibitors of tumorogenic viruses and their functions an important undertaking in the effect to treat cancer.

3. Prior Art

Guanine derivatives with antiviral activity are disclosed in Synthetic Communications 2 (6), 345-351 (1972), U.S. Pat. No. 4,199,574, U.S. Pat. No. 4,355,032, European Patent Application publ. number 74,306, European Patent Application publ. number 55,239; the latter discloses the antiviral compound 9-(3,4-dihydroxybutyl)guanine. By European Patent Application publ. number 108285 are purine derivatives with a hydrogen atom in the 6-position and with an acyclic chain in the 9-position and having antiviral activity previously described.

DISCLOSURE OF THE INVENTION

The present invention relates to novel compounds of the formula wherein
$R_1$ is hydrogen or hydroxymethyl;
$R_2$ is hydrogen, hydroxy or hydroxymethyl;
$R_3$ is hydrogen; or $R_1$ and $R_3$ together constitute an additional carbon-carbon bond;
with the proviso that when $R_1$ is hydrogen then $R_2$ is hydroxy or hydroxymethyl, that when $R_1$ is hydroxymethyl then $R_2$ is hydrogen and that when $R_2$ is hydroxy then $R_1$ is hydrogen; and physiologically acceptable salts, geometric or optical isomers thereof.

The invention also relates to a novel method for combating virus infections in animals and man, compounds for use in such treatment and novel pharmaceutical preparations containing a compound of the formula I.

It has now been found that the compounds of the invention exert an antiviral effect and inhibit certain viral functions including tumorogenic functions and the multiplication of viruses. Some 2-aminopurine compounds having in the 6-position a hydrogen atom and in the 9-position being substituted by (R)-3,4-dihydroxybutyl, 4-hydroxy-3-(hydroxymethyl)butyl, 4-hydroxy-2-(hydroxymethyl)butyl, cis-4-hydroxy-2-butenyl or 4-hydroxy-3-(hydroxymethyl)-2-butenyl side chains, in vivo, on a molar basis, are more potent than the corresponding 6-hydroxy compounds. These 6-hydrogen compounds are oxidized in vivo to the 6-hydroxy compounds and have much higher solubility both in lipid solvents (like 1-octanol) and in water. These 6-hydrogen compounds also have better absorption and penetration properties than their 6-hydroxy analogues. Their in vivo metabolism to the 6-hydroxy analogues makes them efficient prodrugs and give enhanced concentration of these antiviral compounds.

The invention thus provides compounds, stereo-isomers and physiologically acceptable salts thereof, which compounds are useful in therapeutic and/or prophylactic treatment of viral diseases and which may be useful in therapeutic and/or prophylactic treatment of cancer caused by viruses.

An effective selective antiviral agent with acceptable side effects should have a selective inhibiting effect on a specific viral function of the virus to be combated. It is, therefore, one object of the present invention to provide a novel method for combating virus infections using an antiviral agent which extents a selective inhibiting effect on viral functions but which exerts only a negligible inhibiting effect on functions of the host cells.

An especially important area of use for the compounds of the present invention is in the treatment of herpesvirus infections. Among the herpesviruses may be mentioned Herpes simplex type 1 and 2, varicella (Herpes zoster), virus causing infectious mononucleosis (i.e. Epstein-Barr virus) and cytomegalovirus. Important diseases caused by herpesviruses are herpes dermatitis (including herpes labialis), herpes genitalis, herpes keratitis, herpes encephalitis and herpes zoster.

Another possible area of use for the compounds of the present invention is in the treatment of cancer and tumors, particularly those caused by viruses. This effect may be obtained in different ways, i.e. by inhibiting the transformation of virus-infected cells to a neoplastic state, by inhibiting the spread of viruses from transformed cells to other normal cells and by arresting the growth of virus-transformed cells.

A further area of use for the compounds of the present invention is in the inhibition of transformed cells due to the presence in these cells of specific herpesvirus enzymes like thymidine kinase.

Possible areas of use for the compounds of the present invention with respect to cancer chemotherapy are treatment of leukemias, lymphomas including Burkitt lymphomas and Hodgkin's disease, sarcomas, breast carcinoma, nasopharyngeal carcinomas and cervical cancers in which viruses are indicated. Other possible areas of use for the compounds of the present invention with respect to cancer chemotherapy are treatment of multiple myeloma and cancer of the lungs (and bronchus), the stomach, the liver, the colon, the bladder, the lips, the bones, the kidneys, the ovary, the prostate, the pancreas, the skin (melanoma), the rectum, the salivary glands, the mouth, the esophagus, the testis, the brain (and cranial meninges), the thyroid gland, the gallbladder (and ducts), the nose, the larynx, connective tissues, the penis, the vulvas, the vagina, the corpus uteri and the tongue.

The invention furthermore provides

A. A method for the treatment of diseases caused by viruses in animals including man, comprising administering to an animal so infected a therapeutically effective amount of a compound of the formula I or a physiologically acceptable salt thereof.

B. A method for inhibiting the multiplication of virus, in particular herpesviruses, in animals including man, by administering to an animal in need of such treatment a compound of the formula I or a physiologically acceptable salt thereof in an amount sufficient for inhibiting said multiplication.

C. A method for the treatment of virus-induced neoplastic diseases in animals including man, by inhibiting the growth of cells expressing viral functions, characterized by administering to an animal so infected a therapeutically effective amount of a compound of the formula I or a physiologically acceptable salt thereof.

D. A method for inhibiting the growth of virus-transformed cells in animals including man, characterized by administering to an animal in need of such treatment a compound of the formula I or a physiologically acceptable salt thereof in an amount sufficient for inhibiting said growth.

E. A method for the treatment of virus-induced neoplastic diseases in animals including man, by inhibiting the multiplication of tumor viruses, characterized by administering to an animal in need of such treatment a compound of the formula I or a physiologically acceptable salt thereof in an amount sufficient for inhibiting such multiplication.

F. A method for the treatment of neoplastic diseases in animals including man, characterized by administering to an animal a therapeutically effective amount of a compound of the formula I or a physiologically acceptable salt thereof.

The invention also relates to the use of a compound of the formula I or a physiologically acceptable salt, geometric or optial isomer thereof, in each of the above given methods, A, B, C, D, E and F.

As stated previously the novel compounds of the present invention have the formula wherein
$R_1$ is hydrogen or hydroxymethyl;
$R_2$ is hydrogen, hydroxy or hydroxymethyl;
$R_3$ is hydrogen; or $R_1$ and $R_3$ together constitute an additional carbon-carbon bond;
with the proviso that when $R_1$ is hydrogen then $R_2$ is hydroxy or hydroxymethyl, that when $R_1$ is hydroxymethyl then $R_2$ is hydrogen and that when $R_1$ is hydroxy then $R_1$ is hydrogen; or physiologically acceptable salts, geometric or optical isomers thereof.

The proviso in the definition for the growth groups $R_1$ and $R_2$ above mean that the following specific compounds, including salts, geometric and optical isomers thereof, constitute part of the present invention;

2-amino-9-[4-hydroxy-3-(hydroxymethyl)butyl]-9H-purine 2-amino-9-(4-hydroxy-3-hydroxymethyl-2-butenyl)-9H-purine cis-2-amino-9-(4-hydroxy-2-butenyl)-9H-purine 2-amino-9-[4-hydroxy-2-(hydroxymethyl)butyl]-9H-purine (R)-2-amino-9-[4-hydroxy-2-(hydroxymethyl)butyl]-9H-purine (S)-2-amino-9-[4-hydroxy-2-(hydroxymethyl)butyl]-9H-purine (R)-2-amino-9-(3,4-dihydroxybutyl)-9H-purine The compounds of formula I contain one asymmetric center when $R^1$ is hydroxymethyl or $R^2$ is hydroxy. Accordingly, they exist in two optical forms, which constitute a further aspect of the invention.

Further, when $R^1$ and $R^3$ together form an additional bond and $R^2$ is hydrogen, the compound exists as two geometric isomers.

A preferred group of compounds of the formula I are:

Compounds wherein $R_1$ and $R_3$ are hydrogen, or $R_1$ and $R_3$ together constitute an additional carbon-carbon bond; $R_2$ is hydrogen, hydroxy or hydroxymethyl; with the proviso that when $R_1$ is hydrogen then $R_2$ is hydroxy or hydroxymethyl and that when $R_2$ is hydroxy then $R_1$ is hydrogen.

A preferred compound of the invention is (R)-2-amino-9-(3,4-dihydroxybutyl)-9H-purine. A further preferred compound of the present invention is the compound 2-amino-9-[4-hydroxy-2-(hydroxymethyl)butyl]-9H-purine and especially its use for the treatment of varicella (Herpes zoster) virus.

Methods of Preparation

The compounds of the invention may be obtained by one of the following methods A-F constituting a further aspect of the invention.

A. Deprotecting a 9-substituted purine derivative through one or more chemical reactions.

wherein $R_1$, $R_2$ and $R_3$ are as defined above in the formula I.

$R_4$ is hydrogen or a protecting group of which a great variety is known to those skilled in the art (see for example "Protective Groups in Organic Chemistry", T. W. Greene, Wiley 1981; "Methoden der Organischen Chemie", Houben-Weyl VI/1b; and "Comprehensive Organic Chemistry", D. H. R. Barton and W. D. Ollis eds., 1979, vol. 1. pp. 623-629).

Some examples of $R_4$ are acyl groups such as acetyl or benzoyl, alkoxycarbonyl or aryloxycarbonyl groups, silyl groups as for example tert.-butyldimethylsilyl, arylalkyl such as benzyl and triarylmethyl, or $SO_2R_5$ where $R_5$ is alkyl containing 1-8 carbon atoms, fluorinated alkyl containing 1-8 carbon atoms such as trigluoromethyl, arylalkyl such as benzyl, or aryl.

$R_{1a}$ is $R_1$ or $CH_2OR_4$, where $R_4$ is as defined above; $R_{2a}$ is $R_2$, $OR_4$ or $CH_2OR_4$, where $R_4$ is as defined above, or $R_{1a}$ and $R_{2a}$ may additionally together with $OR_4$ form a divalent group, that is a cyclic derivative such as for example a cyclic ester, orthoacid, acetal, ether or silyl type compound;

$R_6$ and $R_7$ are hydrogen or $R_4$ as defined above.

B. Condensing an acyclic side chain, where the functional groups may optionally be protected, to the N-9 position of a purine derivative, followed by removal of the protecting groups, through one or more chemical reactions.

$R_1$, $R_2$, $R_3$, $R_4$, $R_5$, $R_6$, $R_7$, $R_{1a}$ and $R_{2a}$ are as defined above; X and Y are generally selected from groups being able to react with each other for the formation of an optionally protected compound of the formula I; X is e.g. a group such as chloro, bromo, iodi, or a group $OSO_2R_5$ where

$R_5$ is defined above;

Y is e.g. hydrogen, a quaternary ammonium ion such as tetrabutylammonium, or a metal ion such as Li, Na or K.

The condensation is preferably conducted in an organic solvent such as for example dimethylformamide, ethanol, acetonitrile or dichloromethane, at a temperature of between 0° C. and 100° C. for 1 hour to 3 days in the presence of a base (when Y is H) such as for example potassium carbonate.

After condensation, the compounds are hydrolyzed at 0°-100° C. for 1-24 hours with acid or base such as for example acetic acid, hydrochloric acid (1-35%) in water, sodium hydroxide (1-20%) in water, ammonia (1-25%) in water or methanol, or hydrogenated with hydrogen gas in organic solvent such as for example ethanol or dimethylformamide over a metal catalyst for 1-24 hours at a pressure of 100 to 5000 kPa (1-50 atmospheres).

C. Condensing an unsaturated side chain, where the functional groups may optionally be protected, to the N-9 position of a purine derivative with metal catalysis, followed by removal of the protecting groups, through one or more chemical reactions.

$R_6$ and $R_7$ are as defined above; $R_8$ is hydrogen or $CH_2OH$;

$R_{8a}$ is $R_8$ or $CH_2OR_4$, where $R_4$ and $R_8$ are as defined above.

The condensation is preferably conducted in an organic solvent such as for example dimethylformamide, ethanol, acetonitrile or dichloromethane, at a temperature of between 0° C. and 100° C. for 1 hour to 3 days in the presence of a metal catalyst, such as for example tetrakis(triphenylphosphine)palladium(O).

D. Reduction or selective reduction of a purine derivative in one or more steps, followed by removal of protective groups.

$R_1$, $R_2$, $R_3$, $R_4$, $R_6$ and $R_7$ are as defined above; $R_9$ is hydrogen or X as defined above; $R_{10}$ is $R_{1a}$ as defined above or $COR_{11}$, where $R_{11}$ is X, $OR_4$ or $OR_5$ as defined above or a group such as $(CH_3)_2N^{\oplus}=CHO-$ in an activated carboxylic acid derivative; $R_{12}$ is $R_{2a}$ or $COR_{11}$ as defined above, or $R_{10}$ and $R_{12}$ together constitute an additional carbon-carbon bond, or $R_{10}$ and $R_{12}$ may additionally together with $R_{13}$ form a divalent group, that is a cyclic derivative such as for example a lactone or another cyclic ester, orthoacid, acetal, ether or silyl type compound; $R_{13}$ is $CH_2OR_4$ or $COR_{11}$ as defined above; $R_{14}$ is $R_3$ as defined above and $R_{15}$ is hydrogen, or $R_{14}$ and $R_{15}$ may constitute an additional carbon-carbon bond to form an alkene, or, together with $R_{10}$ and $R_{12}$, an alkyne.

The reductions may be performed by hydrogen gas or hydrogen generated in situ, with a metal as catalyst or a hydrid reducing agent in an organic solvent.

E. Substitution in the pyrimidine ring of a purine for the formation of a 2-aminopurine, followed by removal of protecting groups.

$R_1$, $R_2$, $R_3$, $R_4$, $R_{1a}$ and $R_{2a}$ are as defined above. $R_{16}$ is fluoro or X as defined above. It is substituted by ammonia in an organic solvent such as methanol, from normal to higher pressure at room temperature to 100° C. for 1 to 25 hours or by an azide ion followed by reduction by known methods.

F. Imidazole ring closure of a substituted pyrimidine derivative to the purine base, followed by removal of protecting groups.

$R_1$, $R_2$, $R_3$, $R_4$, $R_{1a}$ and $R_{2a}$ are as defined above; $R_{17}$ is nitroso, nitro, amino, or an amino derivative such as formylamino ($-NH-CHO$) or ortho ester amino (e.g.

).

The ring closure may be performed by known methods (the principles of which are given for example in "Comprehensive Organic Chemistry" p. 499–504, 1979, Vol. 4, D. H. R. Barton and W. D. Ollis eds.).

The ring closure may be performed in an organic solvent such as for example formic acid, formamide, orthoformate ester or diethoxymethyl acetate at a temperature from 25° to 250° C. for 10 minutes to 10 hours. When $R_{17}$ is nitroso or nitro, these groups first have to be reduced to amino groups by known methods. When $R_{1a}$, $R_{2a}$ and $R_4$ are not $R_1$, $R_2$ and hydrogen, respectively, the side chain protecting groups are removed in a subsequent reaction step according to method A.

The described methods A-F may be used to give mixtures of optical isomers, or in appropriate cases a single optical isomer. Additionally a single optical isomer may be obtained from the racemic mixtures by methods known per se.

The described methods A-F may be used to give mixtures of geometric isomers, or in appropriate cases a single geometric isomer. Additionally a single geometric isomer may be obtained from the isomeric mixtures by methods known per se.

The starting materials in the above methods A-F are either known compounds or can be prepared according to methods known to those skilled in the art.

These groups of new compounds can be prepared in a way known per se.

Salts

Physiologically acceptable salts of compounds of the invention are prepared by methods known in the art. The salts are novel compounds and comprise a further aspect of the invention. Metal salts can be prepared by reaction of a metal hydroxide with a compound of the invention. Examples of metal salts which can be prepared in this way are salts containing Li, Na, and K. A less soluble metal salt can be precipitated from a solution of more soluble salt by addition of a suitable metal compound. Acid salts can be prepared by treating a compound of the invention with an acid such as HCl, HBr, $H_2SO_4$, or an organic sulphonic acid.

PHARMACEUTICAL PREPARATIONS

Pharmaceutical preparations of the compounds of the formula

I wherein
$R_1$ is hydrogen or hydroxymethyl;
$R_2$ is hydrogen, hydroxy or hydroxymethyl;
$R_3$ is hydrogen; or $R_1$ and $R_3$ together constitute an additional carbon-carbon bond;
with the proviso that when $R_1$ is hydrogen then $R_2$ is hydroxy or hydroxymethyl, that when $R_1$ is hydroxymethyl then $R_2$ is hydrogen and that when $R_2$ is hydroxy then $R_1$ is hydrogen; or physiologically acceptable salts, geometric or optical isomers thereof, with a pharmaceutically acceptable carrier, constitute a further aspect of the invention.

The compounds of the invention can be administered systemically or locally and will in clinical practice normally be administered topically, orally, intranasally, by injection, by infusion, or by inhalation in the form of a pharmaceutical preparation comprising the active ingredient in the form of the original compound or optionally in the form of a pharmaceutically acceptable salt thereof, in association with a pharmaceutically acceptable carrier which may be a solid, semi-solid or liquid diluent or an ingestible capsule, and such preparations comprise a further aspect of the invention. The compounds may also be used without carrier material. As examples of pharmaceutical preparations may be mentioned tablets, solutions, drops, such as nasal drops, eye drops, preparations for topical application such as ointments, jellies, creams and suspensions, aerosols for inhalation, nasal spray, liposomes, etc. Usually the active substance will comprise between 0.01 and 99% by weight of the preparation, for example between 0.5 and 20% for preparations intended for injection and between 0.1 and 50% for preparations intended for oral administration.

The preparations are preferably in unit dosage form.

To produce pharmaceutical preparations in the form of dosage units for oral application containing a compound of the invention the active ingredient may be mixed with a solid, pulverulent carrier, for example lactose, saccharose, sorbitol, mannitol, a starch such as potato starch, corn starch, amylopectin, cellulose, a cellulose derivative or gelatine and also may include lubricants such as magnesium or calcium stearate or polyethylene glycol waxes and compressed to form tablets or cores for dragées. If dragées are required, the cores may be coated for example with concentrated sugar solutions which may contain gum arabic, talc and/or titanium dioxide, or alternatively with a film forming agent. Dyestuffs can be added to these coatings, for example, to distinguish between different contents of active substance. For the preparation of soft gelatine capsules consisting of gelatine and, for example, glycerol and a plasticizer, or similar closed capsules, the active substance may be admixed with polyethylene glycols or a suitable oil as e.g. sesame oil, olive oil, or arachis oil. Hard gelatine capsules may contain granulates of the active substance with solid, pulverulent carriers such as lactose, saccharose, sorbitol, mannitol, starches (for example potato starch, corn starch or amylopectin), cellulose, cellulose derivatives or gelatine, and may also include magnesium stearate or stearic acid as lubricants.

By using several layers of the active drug, separated by slowly dissolving coatings controlled release tablets on micro beads are obtained. Another way to obtain controlled release is to divide the dose of the active drug into granules with coatings of different thicknesses and fill the granules in hard gelatine capsules or compress into tablets together with the carrier substance. The active substance can also be incorporated in slowly dissolving tablets made for instance of fat and wax substances or evenly distributed in a tablet of an insoluble substance such as physiologically inert plastic substance.

Liquid preparations for oral application may be in the form of elixirs, syrups or suspensions, for example solutions containing from about 0.1% to 20% by weight of active substance, sugar and a mixture of ethanol, water, glycerol, propylene glycol and optionally aroma, saccharine and/or carboxymethylcellulose as a dispersing agent.

For parenteral application by injection preparations may comprise an aqueous solution of the active drug or a physiologically acceptable salt thereof, desirably in a concentration of 0.05-10%, and optionally also a stabilizing agent and/or buffer substances in aqueous solution. Dosage units of the solution may advantageously be enclosed in ampoules.

For topical application, especially for the treatment of herpes virus infections on skin, genitals and in mouth and eyes, the preparations are suitably in the form of a solution, ointment, gel, suspension, cream or the like. The amount of active substance may vary, for example between 0.05–20% by weight of the active substance. Such preparations for topical application may be prepared in known manner by mixing the active substance with known carrier materials such as isopropanol, propylene glycol, glycerol, paraffin, stearyl alcohol, polyethylene glycol, et. The pharmaceutically acceptable carrier may also include a known chemical absorption promoter. Examples of absorption promoters are e.g. azone, dimethylacetamide (U.S. Pat. No. 3,472,931), trichloroethanol or trifluoroethanol (U.S. Pat. No. 3,891,757), certain alcohols and mixtures thereof (British Pat. No. 1,001,949).

The dosage at which the active ingredients are administered may vary within a wide range and will depend on various factors such as for example the severity of the infection, the age of the patient, site of administration etc., and may have to be individually adjusted. As a possible range for the amount of the compounds of the invention which may be administered per day may be mentioned from about 0.1 mg to about 2000, or preferably from 1 mg to about 2000 mg for topical administration, from 50 mg to about 2000 mg or from 100 to about 1000 mg for oral administration and from 10 mg to about 2000 mg or from 50 to about 500 mg for injection.

In severe cases it may be necessary to increase these doses 5-fold to 10-fold. In less severe cases it may be sufficient to use up to 500 or 1000 mg.

The pharmaceutical compositions containing the active ingredients may suitably be formulated so that they provide doses within these ranges either as single dosage units or as multiple dosage units.

Thus, it has been found according to the invention that the compounds of the formula I and the physiologically acceptable salts thereof can be used to inhibit herpes virus multiplication. The compounds of the formula I and physiologically acceptable salts thereof are useful in therapeutic and/or prophylactic treatment of virus infections.

A preferred aspect of the invention is the use of the compounds of the formula I or a physiologically acceptable salt, geometric or optical isomer thereof, in the treatment of herpes virus infections.

WORKING EXAMPLES

The following examples illustrates the preparation of compounds according to the invention.

EXAMPLE 1

(R)-2-Amino-9-(3,4-dihydroxybutyl)purine

VSA 305

A mixture of (R)-4-(2-amino-6-chloropurin-9-yl)-$O^1,O^2$-isopropylidenebutane-1,2-diol (0.50 g), anhydrous sodium acetate (0.35 g), palladium catalyst (10% on carbon, 0.25 g), and 70 ml of anhydrous ethanol was hydrogenated at a pressure of 3 atm. in a Parr apparatus for 18 hours at room temperature. After filtration, the solution was evaporated in vacuum to afford crude (R)-4-(2-aminopurin-9-yl)-$O^1,O^2$-isopropylidenebutane-1,2-diol in quantitive yield.

UV spectrum,$\lambda_{max}$ (nm): 0.1 M HCl 314 (248), H$_2$O (pH 7) 304 (242), 0.1 M NaOH 304 (~242 infl.)

$^1$H NMR (DMSO-d$_6$): δ1.24 and 1.30 (2s) C(CH$_3$)$_2$; 2.02 (m) N—C—CH$_2$; 3.47 (+),~4.00 (m) and ~4.15 (m) NCH$_2$ and CHCH$_2$; 6.51 (broad s) NH$_2$; 8.07 (s) H8; 8.56 (s) H6.

$^{13}$C NMR (DMSO-d$_6$): δ25.77 and 27.05 2CH$_3$; 33.21 N—C—CH$_2$; 39.9 NCH$_2$; 68.50 OCH$_2$; 73.34 OCH; 108.47 $\underline{C}$(CH$_3$)$_2$; 127.35 C5; 143.04 C8; 149.22 C6; 153.28 $\overline{C}$4; 160.75 C2.

VSA 300

Deprotection

A solution of crude (R)-4-(2-aminopurin-9-yl)-$O^1,O^2$-isopropylidenebutane-1,2-diol (0.70 g) in 40 ml of 0.1 M aqueous hydrochloric acid was kept at room temperature for 2 h and then at 50° C. for 5 h, evaporated to dryness in vacuum, and the residue dissolved in water, neutralized with aqueous ammonia, and lyophilized. The product was repeatedly extracted with warm chloroform-methanol 1+1 (by volume) and the combined extracts evaporated to dryness in vacuum to afford (R)-2-amino-9-(3,4-dihydroxybutyl)purine.

UV spectrum,$\lambda_{max}$ (nm): 0.1 M HCl 315 (248), H$_2$O (pH 7) 304 (242), 0.1 M NaOH 304 (242 infl.)

$^1$H NMR (DMSO-d$_6$): δ~1.69 and 1.97 (2m, 2H) N—C—CH$_2$; 3.2–3.5 (m, 3H) CHCH$_2$O; 4.15 (m, 2H) NCH$_2$; 6.5 (broad s, 2H) NH$_2$; 8.02 (s, 1H) H8; 8.56 (s, 1H) H6.

—C NMR (DMSO-d$_6$):δ33.74 N—C—CH$_2$; 40.07 N—CH$_2$; 66.10 CH$_2$O; 68.94 CHO; 127.27 $\overline{C}$5; 143.47 C8; 149.29 C6; 153.35 C4; 160.79 C2.

The starting material (R)-4-(2-amino-6-chloropurin-9-yl)-$O^1,O^2$-isopropylidenebutane-1,2-diol was prepared as follows:

1) (R)-1,2,4-Butanetriol (R)-Dimethyl malate (1.62 g, 10 mmol), prepared according to Boger, D. L. and Panek, J. S., J. Org. Chem. 1981, 46, 1208–10, was dissolved in THF (10 ml) and added dropwise to a prewarmed suspension of lithium aluminium hydride (0.63 g, 16.5 mmol) in THF (15 ml). The reaction mixture was stirred over night at 55° C. After sequential addition of water (0.62 ml), 10% sodium hydroxide (1.20 ml) and water (1.90 ml) the mixture was filtered and the solid residue was boiled twice with THF (2×20 ml) and filtered. The combined filtrates were pooled and evaporated under reduced pressure (13 Pa, 30° C.) leaving crude 1,2,4-butanetriol (0.7 g, 6.6 mmol, 66%).

b) (R)-isopropylidenebutane-1,2,4-triol (R)-(+)-1,2,4-Butanetriol (0.7 g, 6.6 mmol), prepared as described in step a) above, was stirred for 1.5 h in acetone (50 ml) containing 3 drops of conc. perchloric acid, a satured solution of sodium bicarbonate in water (5 ml) was added and the stirring was continued for additional 10 min. The precipitate was filtered off and the filtrate evaporated under reduced pressure (2.7 kPa, 30° C.). The residue was taken up in ethyl acetate, washed with saturated aqueous sodium bicarbonate (5 ml) and brine (5 ml), and dried over magnesium sulphate. Evaporation of the solvent and distillation gave the title compound as a colourless oil (0.3 g, 2.05 mmol, 31%): b.p. 104°–106° C. at ~2.7 kPa. $n_D^{20}=1.4390$.

c) (R)-4-Bromo-isopropylidenebutane-1,2-diol

(R)-Isopropylidenebutane-1,2,4-triol (0.3 g, 2.05 mmol) and triphenylphosphine (0.63 g, 2.4 mmol) were dissolved in methylene chloride (5 ml) and cooled to 0° C. and N-bromosuccinimide (0.38 g, 2.16 mmol) was added in small portions with stirring. After additional 1 h of stirring at 0° C. hexane (15 ml) was added and the resulting precipitate was removed by filtration and washed twice with hexane (2×5 ml). The combined hexane solution was passed through a short column of silica gel (5 g). Elution with hexane (15 ml) gave after evaporation and distillation the title compound as a colourless oil (0.2 g, 0.96 mmol, 47%): b.p. 74°–76° C. at 2.7 kPa (20 mm Hg), $n_D^{20}=1.4630$. $\{\alpha\}_D^{20}=+27.7°$ (c=20, CHCl₃).

d) (R)-4-(2-Amino-6-chloropurin-9-yl)-O¹,O²-isopropylidene-butane-1,2-diol 2-amino-6-chloropurine (162 mg, 0.96 mmol), (R)-4-bromoisopropylidenebutanediol )200 mg, 0.96 mmol) and potassium carbonate (132 mg) were mixed in DMF (10 ml). After stirring for 16 h the reaction mixture was filtered through celite and the solvent evaporated under reduced pressure [13 Pa (0.1 mm Hg), 50° C.]. The residue was triturated with warm chloroform (5 ml) and undissolved material was filtered off. Evaporation of the solvent gave a pale yellow crystalline solid consisting mainly of the 9- and 7-isomers. These were separated by silica gel flash chromatography. Elution with chloroform/methanol (15:1) gave the title compound in pure form (106 mg, 0.36 mmol, 37%): m.p. 129°–30° C., $[\alpha]_D^{21}=+57.5°$ (c=6.97, CHCl₃).

EXAMPLE 2

2-(2-Aminopurin-9-yl)methyl butan-1,4-diol

To a solution of crude dimethyl (2-aminopurin-9-ylmethyl) succinate (3.2 g, 10.9 mmol), dissolved in tert. butanol (250 ml) at 40° C., was added lithium borohydride (1.3 g, 60 mmol) in portions with stirring. After 1 h at ambient temperature, water (30 ml) was added slowly and stirring continued overnight. Inorganic salts were filtered and the solution was evaporated to dryness. Yield of crude product was 1.6 g (50%). Chromatography on silica (chloroform+methanol 7+1) afforded a pure product.

¹H NMR (DMSO-d₆):δ1.4·(m, 2H) CH₂CH₂OH; 2.14 (m, 1H) CH; 3.33(d, 2H)CH-C$\underline{H}_2$OH; 3.44 (diffuse q, 2H); 4.05 (AB part of ABX, 2H) N-CH₂; 6.37 (broad s, 2H) NH₂; 7.99 (s, 1H) H8; 8.56 (s, 1H) H6.

¹³C NMR (D₂O):δ33.11 CH₂CH₂OH; 39.58 CH; 46.34 NCH₂; 61.35 and 63.51 2×CH₂OH; 128.41 C5; 146.92 C8; 150.48 C6; 155.05 C4; 161.50 C2.

The starting material dimethyl 2-(2-aminopurin-9-ylmethyl) succinate was prepared as follows:

a) Dimethyl 2-(2-amino-6-chloropurin-9-ylmethyl)-succinate

A mixture of 2-amino-6-chloropurine (4.07 g, 0.024 mol), dimethyl itaconate (5.00 g, 0.032 mol), and sodium hydride (55% in oil, 0.2 g) in 50 ml of dry dimethylformamide was stirred at room temperature for 3 days. About 50 ml of water was added and the mixture was washed with n-hexane (2×50 ml) and then extracted with 2×50 ml of dichloromethane. The combined CH₂Cl₂ extracts were washed with 2×20 ml of water, dried with magnesium sulfate, and evaporated in vacuum. Treatment with ether and drying afforded a white crystalline produce. Chromatography (silica gel, chloroform+methanol 15+1) yielded 5.54 g (71%) or recrystallization (MeOH-H₂O) yielded 5.15·g (66.1%) of dimethyl 2-(2-amino-6-chloropurin-9-ylmethyl) succinate.

UV spectrum in EtOH,λ$_{max}$ (nm); 310 (247).

¹NMR (CDCl₃) δ2.67 (dd, 2H) CH₂COO; 3.46 (m, 1H) CH;3.70 (2s, 2×3H) OCH₃; 4.42 (ABX system, $J_{gem}$-14 Hz, 2H) NCH₂;5.35 (broad s, 2H) NH₂; 7.79 (s, 1H) H₈.

b) Dimethyl 2-(2-aminopurin-9-ylmethyl) succinate

A mixture of dimethyl 2-(2-amino-6-chloropurin-9-ylmethyl) succinate (3.28 g, 10 mmol), sodium acetate (1.5 g) and 5% palladium on charcoal (0.4 g) in ethanol (200 ml) was hydrogenated with agitation in a Parr apparatus at 40 psi for 116 h/ room temperature. After filtration, sodium acetate (1.6 g) and 5% Pd/C (0.4 g) were added and the hydrogenation was continued for 70/h. After filtration and evaporation to dryness, the residue was extracted with 2×50 ml of chloroform and the combined extracts were evaporated to dryness affording 2.6 g (89%) of crude dechlorinated product.

¹H NMR (DMSO-d₆): 8.00 (s, 1H) H8; 8.56 (s, 1H) H6.

The following examples illustrate the preparation of pharmaceutical compositions of the invention. The wording "active substance" denotes a compound according to the present invention or a salt thereof.

| Tablets | | |
|---|---|---|
| Each tablet contains: | | |
| Active substance | 20.0 | mg |
| Maize starch | 25.0 | mg |
| Lactose | 190.0 | mg |
| Gelatin | 1.5 | mg |
| Talc | 12.0 | mg |
| Magnesium stearate | 1.5 | mg |
| | 250.0 | mg |
| Tablets | | |
| Each tablet contains: | | |
| Active substance | 100.0 | mg |
| Starch | 60.0 | mg |
| Lactose | 190.0 | mg |
| Polyvinylpyrrolidone | 5.0 | mg |
| Magnesium stearate | 5.0 | mg |
| | 360.0 | mg |
| Hard gelatine capsules | | |
| Active substance | 100.0 | mg |
| Starch | 100.0 | mg |
| Magnesium stearate | 2.0 | mg |
| Soft gelatine capsules | | |
| Active substance | 100.0 | mg |
| Polyethylene glycol 400 | 100.0 | mg |
| Suppositories | | |
| Each suppository contains: | | |
| Active substance | 20.0 | mg |
| Ascorbyl palmitate | 1.0 | mg |
| Suppository base | | |
| (Imhausen H or Witepsol ® H) ad | 2000.0 | mg |
| Syrup | | |
| Active substance | 0.200 | g |
| Liquid glucose | 30.0 | g |
| Sucrose | 50.0 | g |
| Ascorbic acid | 0.1 | g |
| Sodium pyrosulfite | 0.01 | g |
| Disodium edetate | 0.01 | g |
| Orange essence | 0.025 | g |
| Certified colour | 0.015 | g |
| Purified water ad | 100.0 | g |
| Injection solution | | |
| Active substance | 3.000 | mg |
| Sodium pyrosulfite | 0.500 | mg |
| Disodium edetate | 0.100 | mg |
| Sodium chloride | 8.500 | mg |
| Sterile water for injection ad | 1.00 | ml |
| Sublingual tablets | | |
| Active substance | 5.0 | mg |
| Lactose | 85.0 | mg |
| Talc | 5.0 | mg |
| Agar | 5.0 | mg |
| | 100.0 | mg |
| Jelly | | |
| Active substance | 1.0 | g |
| Methocel ® | 4.0 | g |
| Methyl p-hydroxybenzoate | 0.12 | g |
| Propyl p-hydroxybenzoate | 0.05 | g |
| Sodium hydroxide and hydrochloric acid to pH 6.7 | | |
| Distilled water ad | 100.0 | ml |
| Ointment I | | |
| Active substance | 1.0 | g |
| Cetyltrimethylammoniumbromide | 0.6 | g |
| Stearyl alcohol | 2.25 | g |
| Cetanol | 6.75 | g |
| Liquid paraffin | 17.0 | g |
| Glycerol | 12.0 | g |
| Distilled water ad | 100.0 | g |
| Ointment II | | |
| Active substance | 3.0 | g |
| Polyethylene glycol 1500 | 50 | g |
| Polyethylene glycol 4000 | 15 | g |
| Propylene glycol ad | 100 | g |
| Ointment III | | |
| Active substance | 3.0 | g |
| Sorbitan monoleate | 5.0 | g |
| Petrolatum ad | 100 | g |

-continued

| Ointment IV | | |
|---|---|---|
| Active substance | 5 | g |
| Adeps lanae | 20 | g |
| Tween ® 60 | 4 | g |
| Span ® 40 | 2 | g |
| Paraffin, liquid | 4 | g |
| Propylene glycol | 5 | g |
| Water ad | 100 | g |
| Ointment V | | |
| Active substance | 5 | g |
| Adeps lane | 20 | g |
| Tween ® 60 | 4 | g |
| Span ® 40 | 2 | g |
| Paraffin, liquid | 4 | g |
| Propylene glycol | 5 | g |
| Boric acid | 2 | g |
| Sodium hydroxide to pH 6.5–8 | | |
| Water ad | 100 | g |
| Eye drops I | | |
| Active substance | 0.01–0.03 | g |
| Disodium edetate | 0.01 | g |
| Sodium chloride for isotonia q.s. | | |
| Hydrochloric acid or sodium hydroxide to pH 6.5–8 | | |
| Methocel ® 65 HG 4000 | 0.06 | g |
| Microbiological preservative q.s. | | |
| Sterile water ad | 10 | ml |
| Eye drops II | | |
| Active substance | 0.02 | g |
| Disodium edetate | 0.01 | g |
| Sodium chloride for isotonia q.s. | | |
| Boric acid | 0.01 | g |
| Methocel ® 65 HG 4000 | 0.06 | g |
| preservatives q.s. | | |
| sterile water ad | 10 | ml |
| Eye ointment I | | |
| Active substance | 3 | g |
| Paraffin oil | 19 | g |
| Petrolatum | 78 | g |
| Cream | | |
| Active substance | 3.0 | g |
| Arlaton | 4.0 | g |
| Cetanol | 2.0 | g |
| Stearic acid | 2.0 | g |
| Paraffin oil | 2.0 | g |
| Propylene glycol | 2.0 | g |
| Glycerol | 1.5 | g |
| Methyl p-hydroxybenzoate | 0.06 | g |
| Propyl p-hydroxybenzoate | 0.03 | g |
| Sodium hydroxide | 0.002 | g |
| Hydrochloric acid to pH 8.0 (water phase) | | |
| Distilled water to | 100 | g |
| Jelly | | |
| Active substance | 3.0 | g |
| Methocel ® | 2.45 | g |
| Glycerol | 10.0 | g |
| Tween ® | 0.10 | g |
| Methyl p-hydroxybenzoate | 0.06 | g |
| Propyl p-hydroxybenzoate | 0.03 | g |
| Sodium hydroxide | 0.002 | g |
| Hydrochloric acid to pH 8.0 | | |
| Distilled water to | 100 | g |

BIOLOGICAL TESTS

The inhibiting effect of compounds of the invention on herpes virus was tested using the method described below.

In the following the compound (R)-(+)-9-(3,4-dihydroxybutyl)guanine is denoted VIS 743, the compound (R)-2-amino-9-(3,4-dihydroxybutyl)purine is denoted VSA 305 and Herpes simplex type 2 virus is denoted HSV-2.

Animal Test

I. Treatment of a "systemic" HSV-2 infection in mice with VIS 743 and VSA 305

Mice infected systemically with HSV-2 strain 91075 ($10^4$ pfu infected i.p.) were treated orally with VIS 743 or VSA 305 twice daily for ten days. Treatment started 1 hour post infection. Mortality was determined on several days post infection.

The results are shown in Table 1 and they show that a low dose of VSA 305, 15 mg/kg has effects comparable to a high dose of VIS 743, 30 mg/kg.

TABLE 1

Antiviral effect of VSA 305 on systemic HSV-2 infection (i.p.) in mice

| Treatment | (mg/kg/day) | Mortality (%) | | | |
|---|---|---|---|---|---|
| | | day 6 | day 9 | day 12 | day 15 |
| none | | 40 | 92 | 100 | 100 |
| VIS 743 | 15 mg/kg | 40 | 80 | 100 | 100 |
| | 30 mg/kg | 0 | 28 | 45 | 53 |
| VSA 305 | 15 mg/kg | 0 | 45 | 50 | 53 |

II. Plasma concentration of VIS 743 in mice after giving VIS 743 or VSA 305 orally Mice were given VIS 743 or VSA 305 p.o. Each compound was given in a dosage of 15 mg/kg. The plasma concentrations of VIS 743 were determined by analysis on HPLC, 30, 60, 90 and 120 min after dosage. Each concentration was determined as an average of results from two mice.

Figure 1:
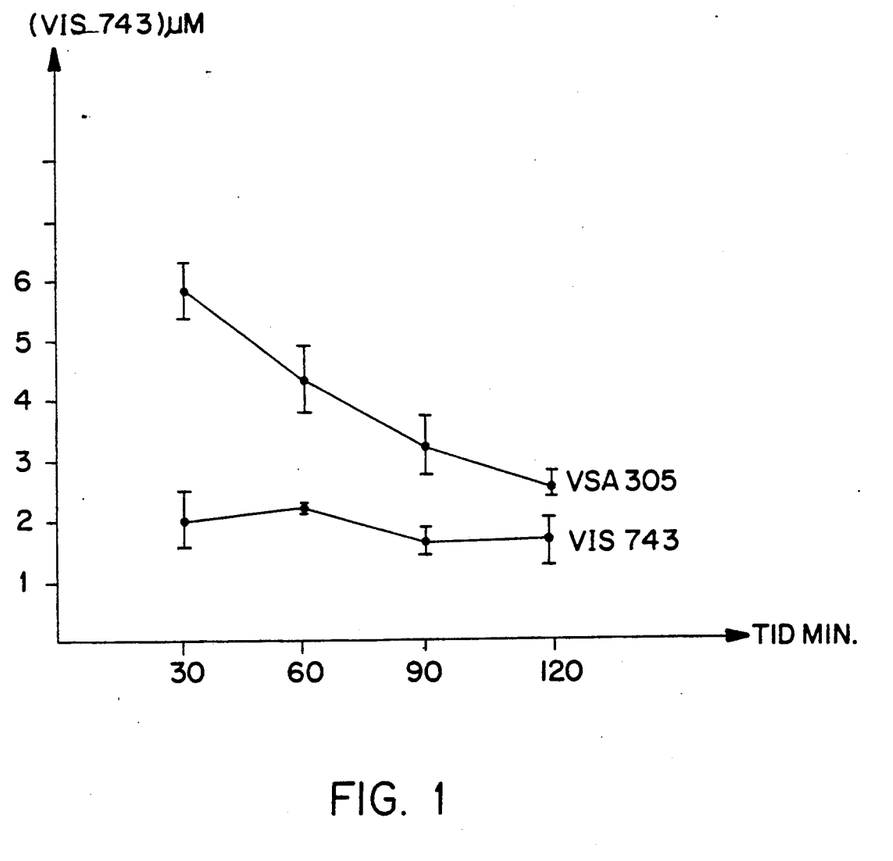
FIG. 1 is a graph showing the plasma concentration of VIS 743 in mice after giving VIS 743 or VSA 305 orally.

The results are shown in FIG. 1 and they show that VSA 305 is biologically transformed to VIS 743 and that by giving VSA 305, up to 3 times higher levels of VIS 743 can be obtained.

What is claimed:

1. A compound of the formula

I wherein
$R_1$ is hydrogen or hydroxymethyl;
$R_2$ is hydrogen, hydroxy or hydroxymethyl;
$R_3$ is hydrogen; or $R_1$ and $R_3$ together constitute an additional carbon-carbon bond;
with the proviso that when $R_1$ is hydrogen then $R_2$ is hydroxy, that when $R_1$ is hydroxymethyl then $R_2$ is hydrogen and that when $R_2$ is hydroxy then $R_1$ is hydrogen; and physiologically acceptable salts, geometric or optical isomers thereof.

2. A compound of the formula

I wherein
$R_1$ and $R_3$ are hydrogen; or $R_1$ and $R_3$ together constitute an additional carbon-carbon bond;
$R_2$ is hydrogen, hydroxy or hydroxymethyl; with the proviso that when $R_1$ is hydrogen then $R_2$ is hydroxy or hydroxymethyl, and that when $R_2$ is hydroxy then $R_1$ is hydrogen; and physiologically acceptable salts, geometric or optical isomers thereof.

3. A compound having the formula 2-amino-9-(4-hydroxy-3-hydroxymethyl-2-butenyl)-9H-purine; and physiologically acceptable salts thereof.

4. A compound having the formula cis-2-amino-9-(4-hydroxy-2-butenyl)-9H-purine; and physiologically acceptable salts thereof.

5. A compound having the formula 2-amino-9-[4-hydroxy-2-(hydroxymethyl)butyl]-9H-purine; and physiologically acceptable salts and optical isomers thereof.

6. A compound having the formula (R)-2-amino-9-(3,4-dihydroxybutyl)-9H-purine; and physiologically acceptable salts thereof.

7. A compound according to one of the claims 1-2 in the form of an optical isomer thereof.

8. A compound according to one of the claims 1-2 in the form of a geometric isomer thereof.

9. A compound according to one of the claims 1-2 in the form of a physiologically acceptable salt thereof.

10. A method for the treatment of virus infections in an animal or human host in need of treatment, comprising administering a therapeutically effective amount of a compound of the formula

I wherein
$R_1$ is hydrogen or hydroxymethyl;
$R_2$ is hydrogen, hydroxy or hydroxymethyl;
$R_3$ is hydrogen; or $R_1$ and $R_3$ together constitute an additional carbon-carbon bond;
with the proviso that when $R_1$ is hydrogen then $R_2$ is hydroxy, that when $R_1$ is hydroxymethyl then $R_2$ is hydrogen and that when $R_2$ is hydroxy then $R_1$ is hydrogen; or physiologically acceptable salts, geometric or optical isomers thereof.

11. A method for treatment of virus infections in an animal or human host in need of treatment, comprising administering a therapeutically effective amount of a compound of the formula

I wherein
$R_1$ and $R_3$ are hydrogen; or $R_1$ and $R_3$ together constitute an additional carbon-carbon bond;

$R_2$ is hydrogen, hydroxy or hydroxymethyl;
with the proviso that when $R_1$ is hydrogen then $R_2$ is hydroxy, and that when $R_2$ is hydroxy then $R_1$ is hydrogen; and physiologically acceptable salts, geometric or optical isomers thereof.

12. A method according to one of the claims 10-11 for the treatment of infections caused by herpes viruses.

13. A method according to one of the claims 10-11 for the treatment of infections caused by varicella (*Herpes zoster*) virus.

14. A method according to one of the claims 10-11 for the treatment of infections caused by Herpes simplex type 1 and 2 virus.

15. A pharmaceutical preparation for use in the treatment of virus in mammals including man comprising an effective amount of a compound of the formula:

I wherein
$R_1$ is hydrogen or hydroxymethyl;
$R_2$ is hydrogen, hydroxy or hydroxymethyl;
$R_3$ is hydrogen; or $R_1$ and $R_3$ together constitute and additional carbon-carbon bond;
with the proviso that when $R_1$ is hydrogen then $R_2$ is hydroxy that when $R_1$ is hydroxymethyl then $R_2$ is hydrogen and that when $R_2$ is hydroxy then $R_1$ is hydrogen; or physiologically acceptable salts, geometric or optical isomers thereof, in conjunction with a pharmaceutically acceptable carrier.

16. A pharmaceutical preparation for use in the treatment of virus in mammals including man comprising an effective amount of a compound of the formula:

I wherein
$R_1$ and $R_3$ are hydrogen; or $R_1$ and $R_3$ together constitute an additional carbon-carbon bond;
$R_2$ is hydrogen, hydroxy; with the proviso that when $R_1$ is hydrogen then $R_2$ is hydroxy and that when $R_2$ is hydroxy then $R_1$ is hydrogen;
and physiologically acceptable salts, geometric or optical isomers thereof.

17. A pharmaceutical preparation according to one of the claims 15 or 16 designed for systemic administration.

18. A pharmaceutical preparation according to one of the claims 15 or 16 designed for topical administration.

19. A compound having the formula (R)-2-amino-9-[4-hydroxy-2-(hydroxymethyl)butyl]-9H-purine or a physiologically acceptable salt thereof.

20. A pharmaceutical composition comprising:
an antiviral effective amount of the compound of claim 5 or 19; and
a pharmaceutically acceptable carrier therefor.

21. A method for the treatment of a viral infection in an animal or human host in need of treatment comprising:
administering a therapeutically effective amount of the compound of claim 5 or 19, to an animal or human.

22. The method of claim 21, wherein said animal or human is suffering from a viral infection caused by a herpes virus.

23. The method of claim 21, wherein said animal or human is suffering from a viral infection caused by a virus selected from the group consisting of Herpes Simplex type 1, Herpes Simplex type 2 and Varicella Zoster Virus.

* * * * *